US00PP29856P3

(12) United States Plant Patent
Jernigan

(10) Patent No.: US PP29,856 P3
(45) Date of Patent: Nov. 20, 2018

(54) ***GARDENIA* PLANT NAMED '4BELLACJ01'**

(50) Latin Name: *Gardenia jasminoides*
Varietal Denomination: 4BELLACJ01

(71) Applicant: Brian J. Jernigan, Dearing, GA (US)

(72) Inventor: Brian J. Jernigan, Dearing, GA (US)

(73) Assignee: Center for Applied Nursery Research, Inc., Dearing, GA (US)

( * ) Notice: Subject to any disclaimer, the term of this patent is extended or adjusted under 35 U.S.C. 154(b) by 0 days.

(21) Appl. No.: 15/732,478

(22) Filed: Nov. 16, 2017

(65) Prior Publication Data

US 2018/0084688 P1 Mar. 22, 2018

(51) Int. Cl.
*A01H 5/02* (2018.01)

(52) U.S. Cl.
USPC ..... Plt./255
CPC ..... *A01H 5/02* (2013.01)

(58) Field of Classification Search
USPC ..... Plt./255
See application file for complete search history.

*Primary Examiner* — Annette H Para
(74) *Attorney, Agent, or Firm* — James R. Holm

(57) ABSTRACT

A new and distinct *gardenia* plant named '4BELLACJ01' particularly distinguished by compact, dark green growth, dense branching habit and heavy flower production, plants having uniform growth under commercial production practices, and increased tolerance to root diseases, is disclosed.

5 Drawing Sheets

Figure 1:
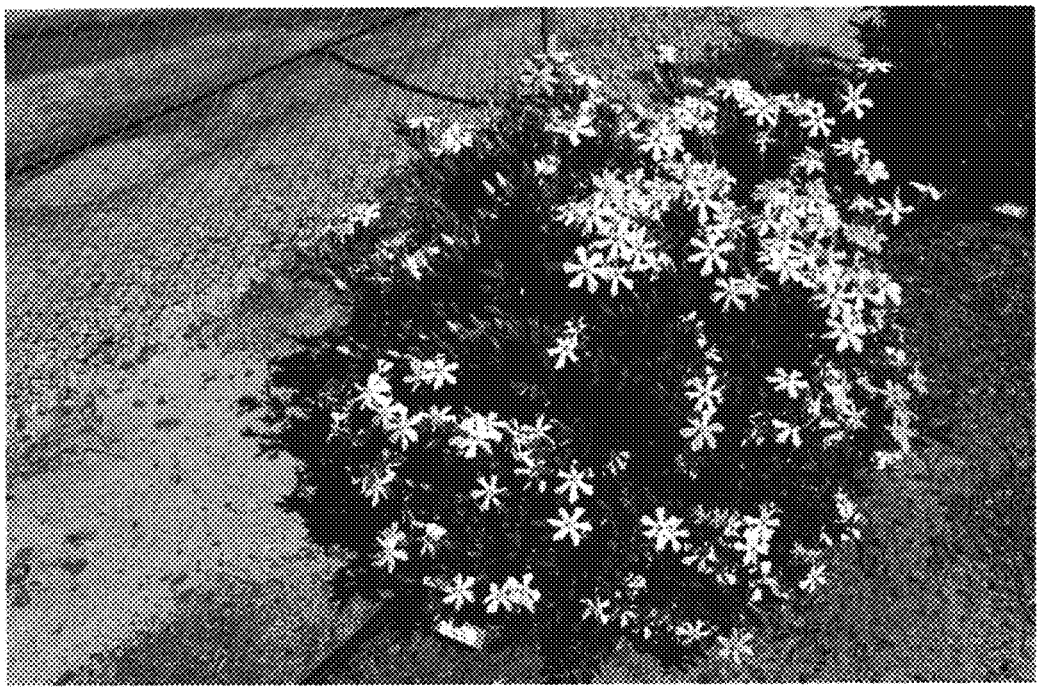

Genus and species: *Gardenia jasminoides.*
Variety denomination: '4BELLACJ01'.

BACKGROUND OF THE NEW PLANT

The present invention comprises a new and distinct variety of *gardenia* plant, botanically known as *Gardenia jasminoides*, and hereinafter referred to by the variety name '4BELLACJ01'. This new *gardenia* plant originated from an open pollination conducted in 2009 in Dearing, Ga. between the female *gardenia* plant 'Frostproof' (unpatented) and an unknown male *gardenia* plant. The objective of the breeding program was to create a new *gardenia* plant with an early blooming habit, compact growth habit, easy-to-grow, and plants exhibiting cold hardiness.

Approximately 1400 progeny seeds resulting from said open pollination were planted in 2009. In 2010, progeny seedlings were planted in 2.5 inch liner cups and then in 2011 progeny seedlings were planted in 1-gallon containers. In 2013, progeny seedlings were planted in 3-gallon containers, inoculated with *Phytophthora cinnamomi*, and grown to evaluate disease response and production characteristics. The new variety was selected by the inventor as a single plant within said progeny in a controlled environment in Dearing, Ga. The new variety was selected based on its response to drought stress, disease, cold hardiness, and unique flowering and growth characteristics. '4BELLACJ01' was first reproduced asexually by vegetative semi-softwood stem cuttings in October 2013 in Dearing, Ga. '4BELLACJ01' has been found to retain its distinctive characteristics and has been found to be stable and reproduce true-to-type through two successive generations of asexual reproduction by vegetative semi-softwood stem cuttings.

Plant Breeder's Rights for this variety have not been applied for. '4BELLACJ01' has not been made publicly available or sold anywhere in the world prior to the effective filing date of this application.

SUMMARY OF THE INVENTION

The new *gardenia* variety has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *gardenia* variety when grown under normal horticultural practices in Dearing, Ga. The combination of these characteristics distinguishes '4BELLACJ01' as a new and distinct variety of *gardenia:*

1. Compact, dark green growth, dense branching habit and heavy flower production;
2. Plants having uniform growth under commercial production practices; and
3. Increased tolerance to root diseases.

DESCRIPTION OF THE PHOTOGRAPHS

This new *gardenia* is illustrated by the accompanying photographs which show the overall plant habit including flowers and foliage of the plant. The colors shown are as true as can be reasonably obtained by conventional photographic procedures. The photographs are of 3.6 to 4-year-old plants and 8-year-old plants grown in the ground and in 3-gallon containers in Dearing, Ga. The photographs were taken in May 2017 in Dearing Ga. under natural light and natural shade. Colors in the photographs may differ slightly from the color values cited in the botanical description which accurately describes the colors of the new variety.

FIG. 1. shows the original seedling and its overall habit, including flowers and foliage.

Figure 2:
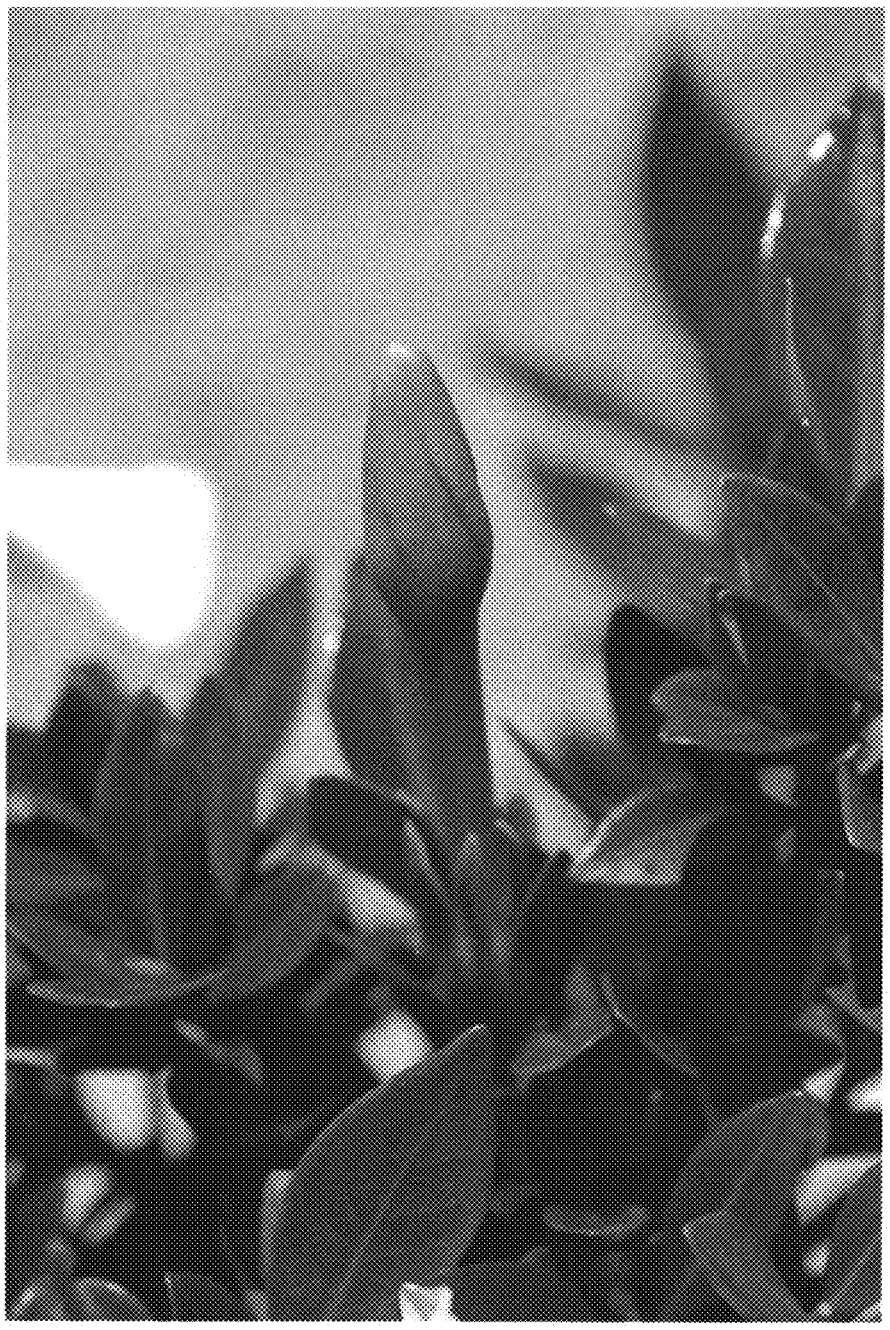

FIG. 2. shows a typical flower bud.

Figure 3:
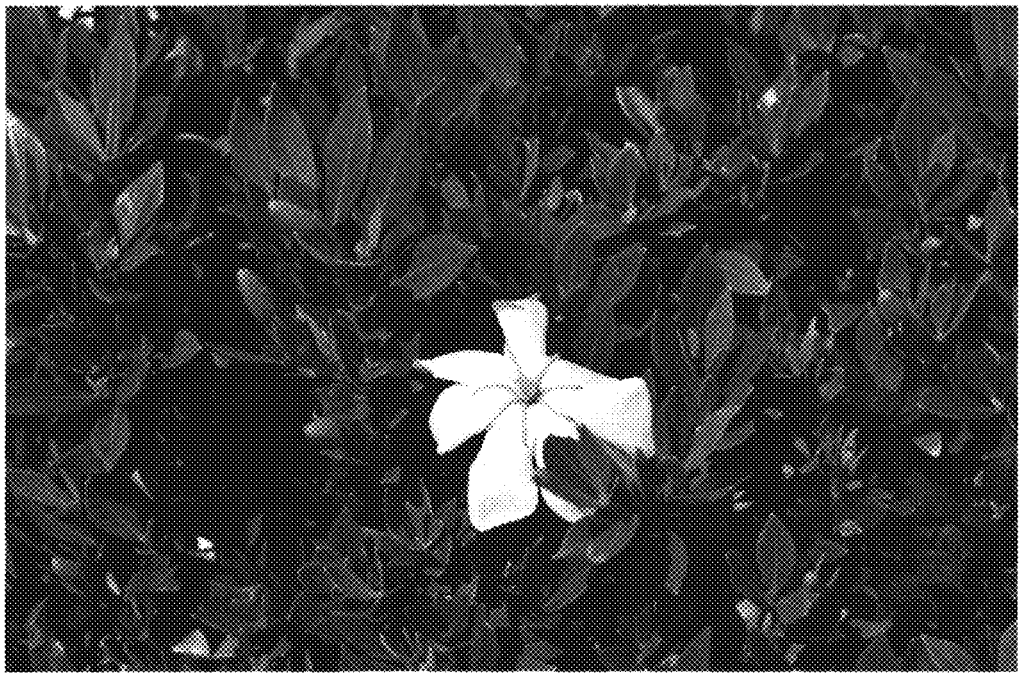

FIG. 3. shows typical foliage, flower buds and a flower.

Figure 4:
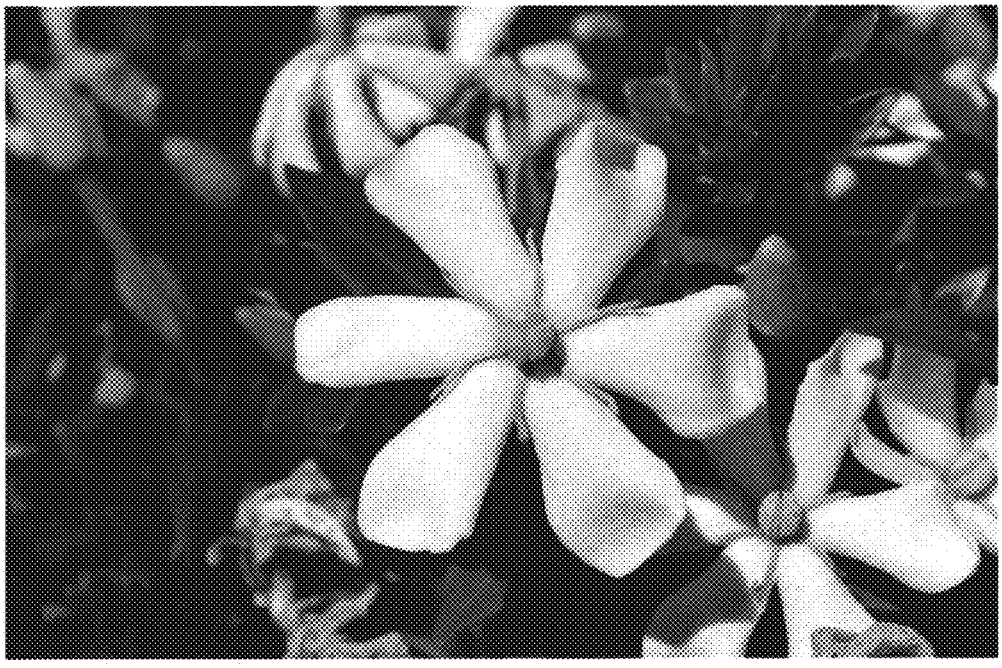
Figure 5:
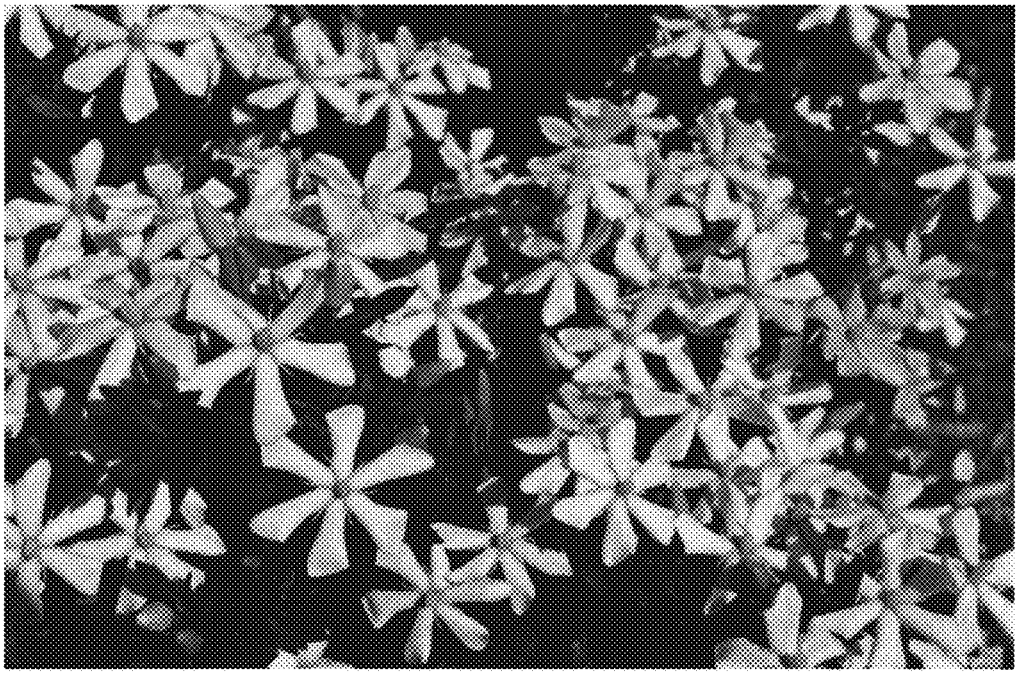

FIG. 4. shows a close up of a mature flower.
FIG. 5. shows flower density.

DESCRIPTION OF THE NEW VARIETY

In the following description, color references are made to The Royal Horticultural Society Colour Chart, Sixth Edition, except where general terms of ordinary dictionary significance are used.

The following observations and measurements describe plants grown in 3-gallon containers when grown outdoors under a natural photoperiod in full sun in Dearing, Ga. Detailed descriptions were taken in 2016 and 2017 from approximately 4-year-old plants grown from single vegetative semi-softwood stem cuttings. Measurements and numerical values represent averages of typical plant types.

DETAILED BOTANICAL DESCRIPTION

Classification:
- *Family*.—Rubiaceae.
- *Botanical*.—*Gardenia jasminoides*.
- *Common*.—*Gardenia*.
- *Denomination*.—'4BELLACJ01'.

Parentage:
- *Female or seed parent*.—*Gardenia jasminoides* plant 'Frostproof' (unpatented).
- *Male or pollen parent*.—Unknown.

Propagation:
- *Type*.—Vegetative semi-softwood stem cuttings.
- *Time to initiate roots*.—14 to 21 days.
- *Time to produce a rooted young plant*.—5 to 6 months, a cutting placed in rooting media in approximately September to October will be rooted and ready to pot in approximately February to March the following year.

Root description: Fibrous.

Plant description:
- *Plant type*.—Evergreen shrub.
- *Growth habit*.—Compact, mounding.
- *Height*.—52.0 cm after 4 years of growth and 95.0 cm after 8 years of growth.
- *Plant spread*.—65.0 cm after 4 years of growth and 120.0 cm after 8 years of growth.
- *Growth rate*.—13.0 cm to 15.0 cm per year depending on environmental conditions and plant's age, growth rate slows as plants mature.
- *Plant vigor*.—Vigorous when young, vigor slows as plants mature.
- *Branching habit*.—Freely branching.
- *Primary branches* (*one year or older*).—Length: 13.5 cm per year. Diameter: 0.4 cm at one year of age. Strength: Pliable during the first year's growth and becoming stiff the second year. Color: Mature branches: Green 139D, grey-brown N199B and greyed-green 197C. Young branches: Grey-brown N199B and green 140B. Texture: No pubescence.
- *Lateral branches* (*less than one year old*).—Length: 4.81 cm per flush. Diameter: 0.2 cm. Strength: Flexible. Aspect: 10 to 45 degree angles from other stems. Texture: Setulose pubescence. Color: Immature branches are yellow-green 144A and maturing to grey-brown 199B, and finally turning yellow-green 144C with exfoliating bark colored grey-brown N199B. Internode length: 1.67 cm.

Foliage description:
- *Leaf type*.—Simple.
- *Leaf arrangement*.—Primarily opposite with some whorled leaves, 2 per node, sometimes 3 per node.
- *Average mature leaf size*.—Length: 2.9 cm. Width: 1.03 cm.
- *Mature leaf shape*.—Oblanceolate.
- *Leaf apex*.—Acuminate.
- *Leaf base*.—Attenuate to crunate.
- *Leaf attachment*.—Petiolate with persistent sheathing stipules at the apex of the node.
- *Leaf margin*.—Entire.
- *Internode length*.—1.75 cm.
- *Leaf texture*.—Upper surface: Glabrous, waxy. Bottom surface: Glabrous.
- *Leaf color*.—Young leaves: Upper surface: Green 143C. Lower surface: Yellow-green 144C. Mature leaves: Upper surface: Green 139A. Lower surface: Green 138B.
- *Leaf venation*.—Type: Pinnate. Color: Green 143C.

Flower description:
- *Bloom period*.—Primary bloom period is typically May in Dearing, Ga., blooming occurs sporadically through summer and fall.
- *Type*.—Perfect flower.
- *Arrangement*.—Single flower at apex of stems and occasionally at leaf axils.
- *Pedicel*.—Length: 0.8 cm. Diameter: 0.2 cm. Color: Yellow-green 144A. Texture: Glabrous. Strength: Slightly pliable, breakable with force.
- *Height* (*depth*).—5.2 cm from attachment to stem.
- *Diameter*.—6.0 cm.
- *Facing direction*.—Outward.
- *Persistence*.—Self-cleaning.
- *Fragrance*.—Typical *gardenia* fragrance.
- *Petals*.—Arrangement: 1 row of petals. Length: 2.5 cm from fusion with the flower tube. Width: 1.6 cm. Apex: Unevenly rounded, oblique. Base: Fused tube. Shape: Obelliptical, obovate. Margin: Entire, slightly wavy and reflexed. Quantity: 6, occasionally 5. Texture: Smooth, glabrous. Color: Upper surface at first opening: 155C. Outer surface at maturity: White NN155D with a strip on the outer petals of white 155A. Inner surface at maturity: White NN155D. Upper and lower surfaces at fading: Yellow 10C and 11B.
- *Buds*.—Shape: Oblong. Length: 3.7 cm. Diameter: 0.7 cm. Color: Yellow-green 144B. Texture: Glaborous.
- *Calyx/sepals*.—Quantity of sepals per flower: 6, occasionally 5. Calyx arrangement: Star-shaped. Sepal shape: Lanceolate and fused to the base. Length of sepals: Extending 1.5 cm beyond calyx. Width of sepals: 0.2 cm at point of fusion to the calyx. Apex: Acute. Base: Fused. Margin: Entire. Texture: Smooth, glabrous. Color: Inner surface: Yellow-green 144B. Outer surface: Yellow-green 144C.

Reproductive organs:
- *Stamens*.—Quantity: 6, occasionally 5. Length: 1.3 cm, no filament, base is fused to petal corona. Width: 0.1 cm. Anthers: Aspect: Lying flat between petals, often recurving slightly. Length: 1.3 cm. Width: 0.1 cm. Color: Greyed-orange 164A and yellow-white 158A, outer surface is greyed-white 156D. Pollen: Amount: Moderate. Color: Yellow 10A.
- *Pistils*.—Quantity: 1 per flower. Length: 4.0 cm. Style: Length: 2.5 cm. Width: 0.1 cm. Color: Yellow 11D.

Stigma: Shape: Obovate with 2 irregular shaped lobes, stigma measure 1.0 cm in length by 0.5 cm in width. Color: Yellow 10D. Ovary: Type: Inferior within calyx cup. Length: 0.2 cm. Diameter: 0.2 cm.

Cold tolerance: Hardy to USDA zone 7 with current evaluations of cold hardiness in USDA zone 6.

Disease and pest tolerance: Tolerance to root diseases has been observed, but not under controlled conditions. Susceptible to insect pests common to *gardenia*, such as scale and whitefly.

Fruit description: Swollen calyx with sepals remaining from flower, fruit measure 2.5 cm in length and 1.5 cm in width, color is yellow-green 144A and becoming orange-red in winter.

Drought tolerance: Tolerance to periodic drought stress has been observed in container grown plants.

COMPARISON WITH PARENTAL VARIETIES

'4BELLACJ01' differs from the female parent plant 'Frostproof' (unpatented) in that '4BELLACJ01' has a denser, more compact branching habit than 'Frostproof'. Additionally, '4BELLAJ01' has single flowers, whereas 'Frostproof' has double flowers.

COMPARISON WITH KNOWN CULTIVARS

'4BELLACJ01' differs from the commercial *gardenia* variety 'PllGA-1' (U.S. Plant Pat. No. 25,510) in that '4BELLACJ01' has a more compact growth habit with plants measuring 52.0 cm by 65.0 cm after 4 years of growth, whereas plants of 'PllGA-1' measure 75.0 cm by 75.0 cm after 5 years of growth. Additionally, leaves of '4BELLACJ01' are narrow oblanceolate, whereas leaves of 'P11GA-1' are elliptical. Furthermore, when compared to 'P11GA-1', '4BELLACJ01' has an improved production consistency under a production setting in Dearing, Ga.

'4BELLACJ01' differs from the commercial *gardenia* variety 'MADGA 1' (U.S. Plant Pat. No. 19,988), in that '4BELLACJ01' has more vigorous growth measuring 52.0 cm by 65.0 cm after 4 years of growth, whereas 'MADGA 1' has growth measuring 23.0 cm by 16.0 cm after 3 years of growth. Additionally, leaves of '4BELLACJ01' are narrow oblanceolate, whereas leaves of 'MADGA 1' are ovate to obovate. Furthermore, when compared to 'MADGA 1', '4BELLACJ01' has an improved production consistency under a production setting in Dearing, Ga.

I claim:

1. A new and distinct variety of *gardenia* plant named '4BELLACJ01', substantially as illustrated and described herein.

* * * * *